US00PP16094P2

(12) United States Plant Patent
Jones

(10) Patent No.: US PP16,094 P2
(45) Date of Patent: Nov. 1, 2005

(54) ***THUJA* PLANT NAMED 'STEEPLECHASE'**

(50) Latin Name: ***Thuja standishii*×*Thuja plicata***
Varietal Denomination: Steeplechase

(75) Inventor: Alan Jones, Felton, PA (US)

(73) Assignee: Manor View Farm, Inc., Monkton, MD (US)

( * ) Notice: Subject to any disclaimer, the term of this patent is extended or adjusted under 35 U.S.C. 154(b) by 10 days.

(21) Appl. No.: 10/849,390

(22) Filed: May 19, 2004

(51) Int. Cl.[7] ..... A01H 7/00
(52) U.S. Cl. ..... Plt./213
(58) Field of Search ..... Plt./213

*Primary Examiner*—Kent Bell
*Assistant Examiner*—Louanne Krawczewicz Myers

(57) ABSTRACT

A new and distinct cultivar of *Thuja* plant named 'Steeplechase', characterized by its broadly pyramidal plant form; dark green-colored leaves; finely-dissected foliage; and dense and bushy appearance.

3 Drawing Sheets

Botanical classification/cultivar designation: *Thuja standishii*×*Thuja plicata* cultivar Steeplechase.

BACKGROUND OF THE INVENTION

The present Invention relates to a new and distinct cultivar of *Thuja*, botanically known as *Thuja standishii*×*Thuja plicata*, and hereinafter referred to by the name 'Steeplechase'.

The new *Thuja* is a naturally-occurring branch mutation of the *Thuja standishi*×*Thuja plicata* cultivar Green Giant, not patented. The Inventor discovered the new *Thuja*as a single branch mutation within a population of plants of the parent 'Green Giant' in a controlled environment in Monkton, Md. during the summer of 1990. The selection of this new *Thuja* was based of its finely-textured foliage.

Asexual reproduction of the new *Thuja* by cuttings in a controlled environment in Monkton, Md., since 1990 has shown that the unique features of this new *Thuja* are stable and reproduced true to type in successive generations.

SUMMARY OF THE INVENTION

Plants of the cultivar Steeplechase have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Steeplechase'. These characteristics in combination distinguish 'Steeplechase' as a new and distinct cultivar of *Thuja:*

1. Broadly pyramidal plant form.
2. Dark green-colored leaves.
3. Finely-textured foliage; dense and bushy appearance.

Plants of the new *Thuja* are most similar to plants of the parent, the cultivar Green Giant. In side-by-side comparisons conducted in Monkton, Md., plants of the new *Thuja* differed from plants of the cultivar Green Giant, in the following characteristics:

1. Plants of the new *Thuja* were shorter and broader than plants of the cultivar Green Giant.

2. Leaves of plants of the new *Thuja* were more finely-textured, looser and darker green in color than leaves of plants of the cultivar Green Giant.
3. Plants of the new *Thuja* were denser and bushier than plants of the cultivar Green Giant.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Thuja.*

The photograph on the first sheet comprises a side perspective view of a typical plant of 'Steeplechase' grown in the landscape.

The photograph on the second sheet comprises a side perspective view of typical plants of 'Green Giant' (left) and 'Steeplechase' (right) grown in the landscape.

The photograph on the third sheet comprises a close-up view of typical branchlets and leaves of 'Steeplechase' (left) and 'Green Giant' (right).

DETAILED BOTANICAL DESCRIPTION

Plants used for the aforementioned photographs and following observations and measurements were grown in Monkton, Md., during the winter in an outdoor nursery and under conditions which approximate commercial *Thuja* production. Plants had been growing for about 13 years when the photographs and description were taken.

In the following description, color references are made to The Royal Horticultural Society Colour Chart, 1995 Edition, except where general terms of ordinary dictionary significance are used.

Botanical classification: *Thuja standishii*×*Thuja plicata* cultivar Steeplechase.

Patentage: Naturally-occurring branch mutation of the *Thuja standishii*×*Thuja plicata* cultivar Green Giant, not patented.

Propagation:

*Type.*—By cuttings.

*Time to initiate roots.*—About two months at 20° C.

*Time to produce a rooted cutting.*—About six months at 20° C.

*Root description.*—Thick, fleshy; white in color.

*Rooting habit.*—Freely branching; dense.

Plant description:

*Form.*—Broadly pyramidal perennial evergreen tree.

*Branching habit and branchlets.*—Freely branching with branches mostly horizontal and branchlets and terminal branchlets (smallest branchlet divisions) borne in the same plane and loosely pendulous towards the apices. Trees maintain their lower branches and foliage to the soil level. Branchlets of current season's growth with scale-like, appressed leaves borne parallel to the axis of the branchlet with alternating facial and lateral leaves. Sprays or terminal branchlets one to two-pinnate with limited overlapping resulting in a loose and open appearance.

*Plant height.*—About 4.6 to 5.2 meters.

*Plant diameter.*—About 1.5 meter.

*Trunk description.*—Length: About 5 meters. Diameter (at soil level): About 23 cm. Texture: Woody. Color: Brown, close to 177A.

*Primary branch description.*—Length: About 70 cm. Diameter: About 5 cm. Texture: Woody. Color: Brown, close to 177A.

*Branchlet and terminal description.*—Length: About 20 cm. Diameter: About 2 cm. Texture: Woody. Color: Brown, close to 177A.

*Branchlet leaf description.*—Appearance: Flattened and appressed. Length: About 5 to 7 mm. Width: About 3 mm. Shape: Ovate. Apex: Bluntly pointed. Margin: Entire. Venation pattern: Linear. Fragrance: When bruised, tansy. Color: Upper surface, winter: 147A. Lower surface, winter: 137B to 137C. Upper surface, summer: 137A. Lower surface, summer: 137D. Venation, upper and lower surfaces: Same as lamina.

*Spray leaf description.*—Appearance: Flattened and appressed. Length: About 2 to 4 mm. Width: About 2 mm. Shape: Ovate. Apex: Bluntly pointed. Margin: Entire. Venation pattern: Linear. Fragrance: When bruised, tansy. Color: Upper surface, winter: 147A. Lower surface, winter: 137B to 137C. Upper surface, summer: 137A. Lower surface, summer: 137D. Venation, upper and lower surfaces: Same as lamina.

Cone description: Cone development has not been observed.

Disease/pest resistance: Plants of the new *Thuja* have not been noted to be resistant to pathogens or pests common to *Thujas.*

Weather tolerance: Plants of the new *Thuja* have been observed to be tolerant to drought, rain, wind and temperatures ranging from −22 to 40° C.

It is claimed:

1. A new and distinct cultivar of *Thuja* plant named 'Steeplechase', as illustrated and described.

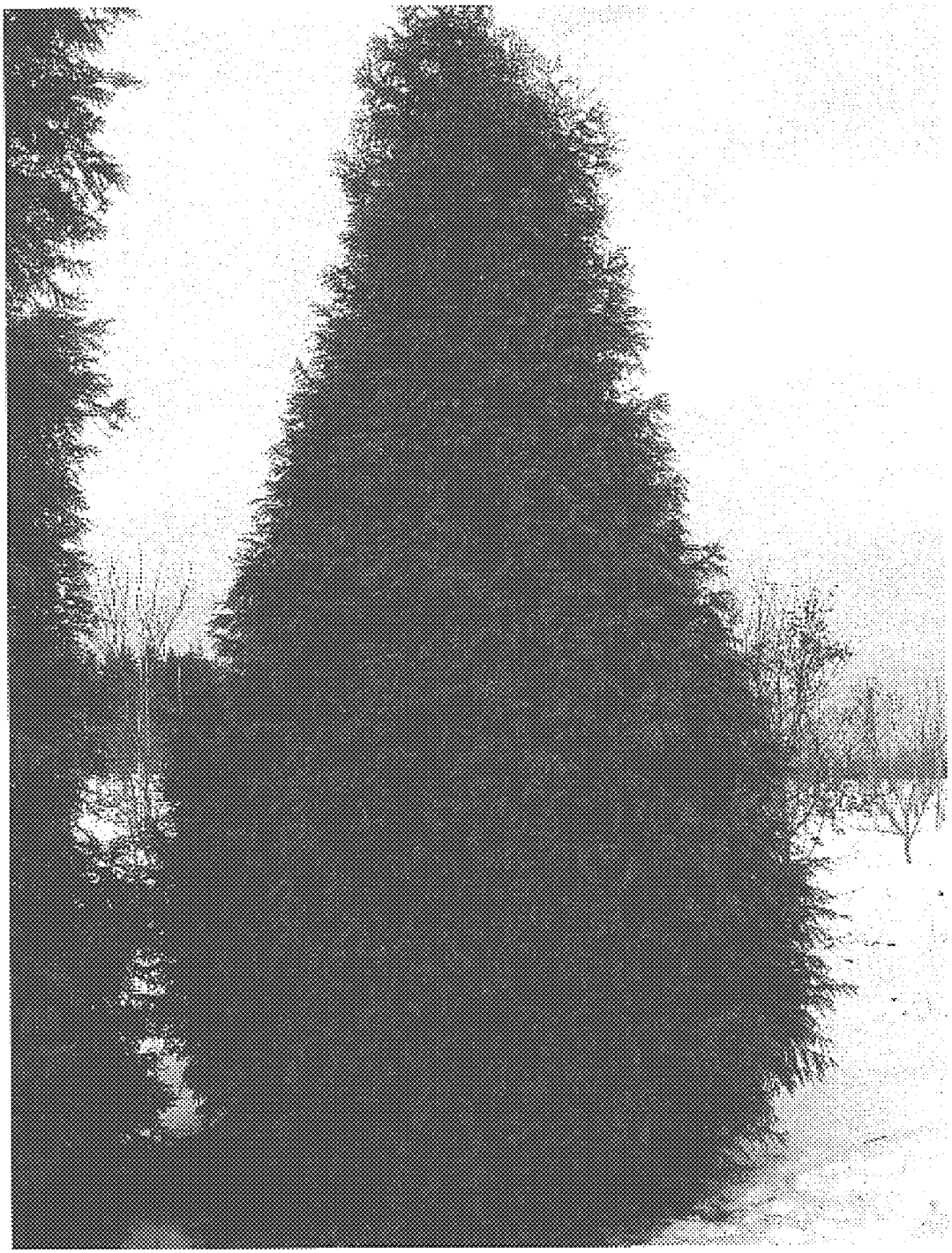

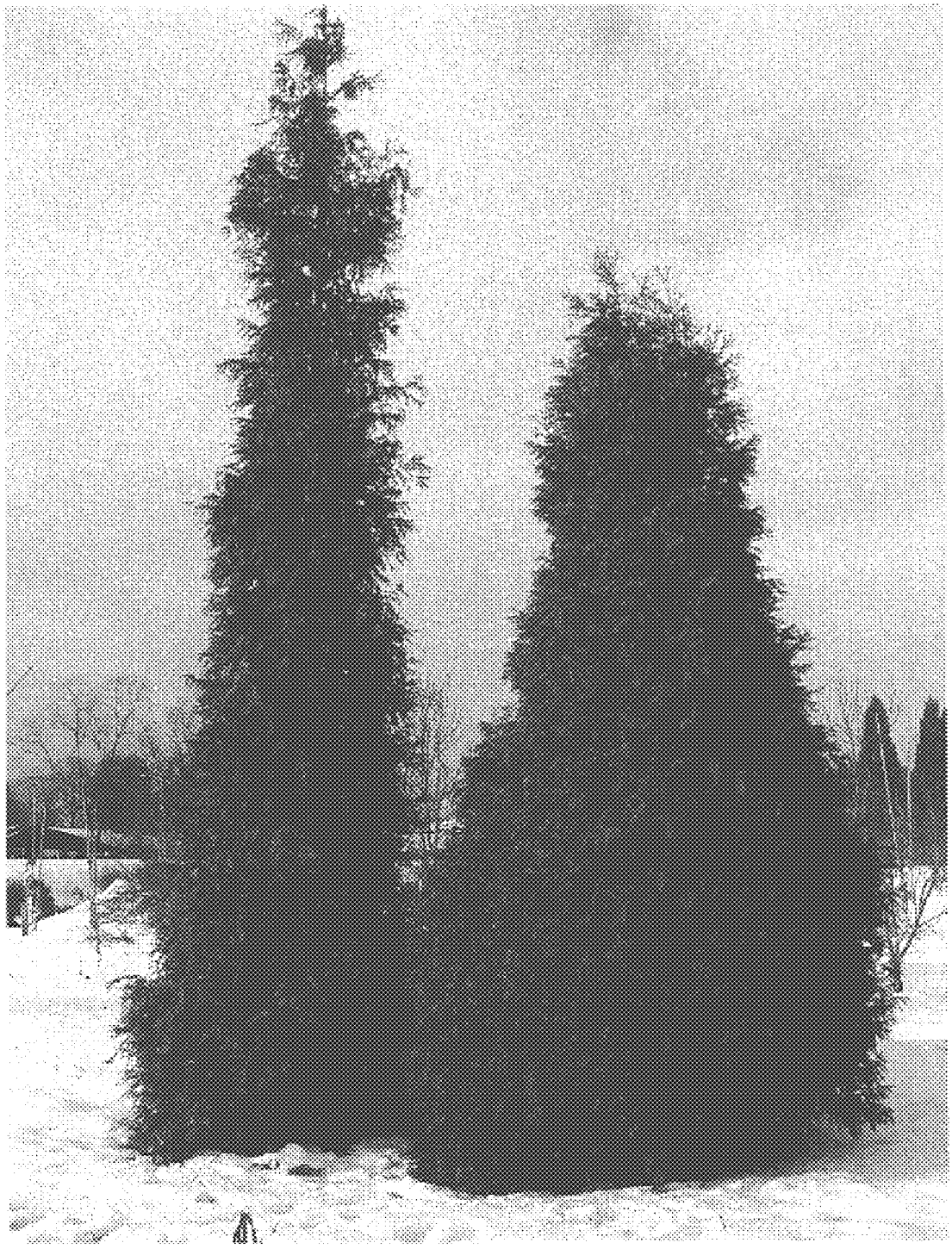

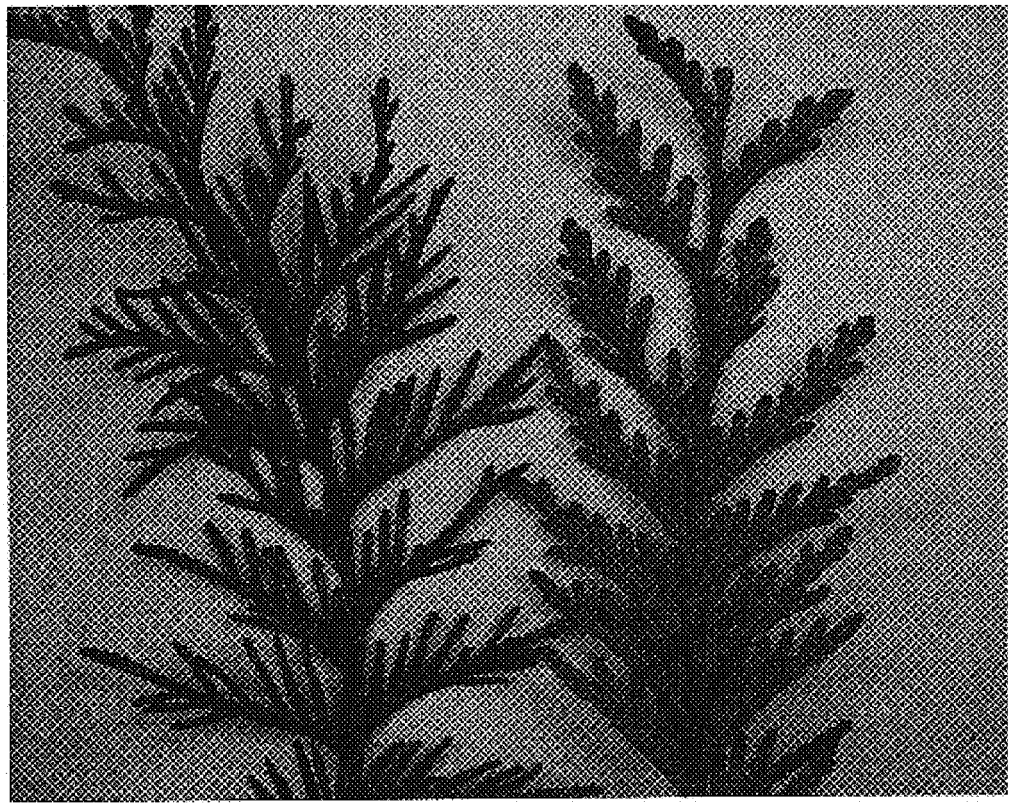

* * * * *